(12) United States Patent
Miller et al.

(10) Patent No.: US 10,976,305 B2
(45) Date of Patent: Apr. 13, 2021

(54) COAGULATION TESTING IN UNDERFILLED PATIENT SAMPLES

(71) Applicant: The University of Chicago, Chicago, IL (US)

(72) Inventors: Jonathan Miller, Chicago, IL (US); Adam Cloe, Chicago, IL (US); Krzysztof Mikrut, Oak Forest, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 228 days.

(21) Appl. No.: 15/965,343

(22) Filed: Apr. 27, 2018

(65) Prior Publication Data

US 2018/0313817 A1 Nov. 1, 2018

Related U.S. Application Data

(60) Provisional application No. 62/490,961, filed on Apr. 27, 2017.

(51) Int. Cl.
| | | |
|---|---|---|
| *G01N 33/49* | (2006.01) | |
| *G01N 33/86* | (2006.01) | |
| *G01N 33/96* | (2006.01) | |

(52) U.S. Cl.
CPC ......... *G01N 33/4905* (2013.01); *G01N 33/86* (2013.01); *G01N 33/96* (2013.01); *G01N 2800/52* (2013.01)

(58) Field of Classification Search
CPC ..... G01N 33/4905; G01N 33/86; G01N 33/96
See application file for complete search history.

(56) References Cited

U.S. PATENT DOCUMENTS

2015/0301018 A1\* 10/2015 Dayel ................. C12Q 1/56
435/13

OTHER PUBLICATIONS

Webster, Craig. "Short coagulation samples. Why does it happen? Why is it a problem?" Obtained by the examiner on May 9, 2020 from <https://www.heftpathology.com/Laboratory-Services/short-coagulation-samples-why-does-it-happen-why-is-it-a-problem.html>. 2012. (Year: 2012).\*

\* cited by examiner

*Primary Examiner* — Christopher Adam Hixson
(74) *Attorney, Agent, or Firm* — Casimir Jones SC; David W. Staple

(57) ABSTRACT

Provided herein are methods for generating an estimated coagulation test result from an underfilled sample tube.

23 Claims, 8 Drawing Sheets

COAGULATION TESTING IN UNDERFILLED PATIENT SAMPLES

CROSS-REFERENCE TO RELATED APPLICATIONS

The present invention claims priority to U.S. Provisional Patent Application 62/490,961, filed Apr. 27, 2017, which is incorporated by reference in its entirety.

FIELD

Provided herein are methods for generating an estimated coagulation test result from an underfilled sample tube.

BACKGROUND

When damage to blood vessels and capillaries occurs, the body controls blood loss via physiological processes referred to as hemostasis. In vivo, hemostasis depends on an interaction between the plasma-based coagulation cascade, platelets, and the vessels themselves. In the clinical laboratory, in vitro analytical assays are available for performing a variety of measurements on samples of blood obtained from the patient, thereby providing useful clinical information with respect to the body's hemostatic capabilities.

Clinicians frequently order coagulation tests, such as the prothrombin time (PT), activated partial thromboplastin time (aPTT), and thrombin time (TT), to assess blood clotting function in patients. These laboratory tests may be helpful in elucidating the cause of unexplained bleeding, and/or may be useful in determining whether or not a subject is eligible for a particular treatment. Of particular note, there are a number of clinical situations, most urgently in the case of patients with recent onset of stroke symptoms, for whom delays in obtaining the results of such coagulation testing can result in denial of anti-thrombotic therapies that might otherwise have resulted in significant amelioration of functional impairment attributable to the stroke.

SUMMARY

Provided herein are methods for generating an estimate of coagulation test results from an underfilled sample tube.

In some embodiments, provided herein are methods for calculating an estimated coagulation test value for an underfilled blood sample, comprising: (a) determining the percent fill of the sample; (b) correcting the sample volume; (c) performing the coagulation test to obtain a determined coagulation test value; (d) applying a percent-fill-dependent correction factor to the determined coagulation test value to generate the estimated coagulation test value.

In some embodiments, the underfilled blood sample has a percent fill of less than 90%. In some embodiments, the underfilled blood sample has a percent fill of 50% to 90% (e.g., 50%, 55%, 60%, 65%, 70%, 75%, 80%, 85%, 90%, or ranges therebetween).

In some embodiments, correcting the sample volume comprises adding aqueous buffer, saline, buffered saline, or other diluent to the sample. In some embodiments, the diluent may include a buffer such as a phosphate buffer, a borate buffer, an acetate buffer, or a citrate buffer, or other common buffers such as bicine, tricine, tris(hydroxymethyl)aminomethane (tris), N-[tris(hydroxymethyl)methyl]-3-aminopropanesulfonic acid (TAPS), 3-[N-tris(hydroxymethyl)methylamino]-2-hydroxypropanesulfonic acid (TAPSO), 2-[4-(2-hydroxyethyl)piperazin-1-yl]ethanesulfonic acid (HEPES), N-[tris(hydroxymethyl)methyl]-2-aminoethanesulfonic acid (TES), piperazine-N,N'-bis(2-ethanesulfonic acid) (PIPES), 2-(N-morpholino)ethanesulfonic acid (MES), or the like. In some embodiments, correcting the sample volume comprises adding imidazole buffered saline to the sample. In some embodiments, imidazole buffered saline comprises about 0.34 g imidazole and about 0.585 g of NaCl per 100 mL of distilled water and is at about pH 7.3. In some embodiments, the diluent comprises between 0.05 g and 1.0 g (e.g., 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, or ranges therebetween) imidazole per 100 mL water. In some embodiments, the diluent comprises between 0.05 g and 1.0 g (e.g., 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, or ranges therebetween) salt (e.g., NaCl, $MgCl_2$, KCl, $CaCl_2$, $NaHSO_4$, etc.) per 100 mL water. In some embodiments, the diluent is pH 6 to ph 8 (e.g., 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, or ranges therebetween). In some embodiments, imidazole buffered saline comprises 0.34 g imidazole and 0.585 g of NaCl per 100 mL of distilled water and is at pH 7.3.

In some embodiments, correcting the sample volume comprises bringing to volume of the sample to 90-110% fill. In some embodiments, correcting the sample volume comprises bringing to volume of the sample to 99-101% fill. In some embodiments, correcting the sample volume comprises bringing to volume of the sample to 100% fill.

In some embodiments, performing the coagulation test comprises determining one or more of prothrombin time (PT), activated partial thromboplastin time (aPTT), thrombin time (TT), fibrinogen level, and international normalized ratio (INR). In some embodiments, the determined coagulation test value is the result obtained by performing the coagulation test as if the corrected sample were a properly filled sample.

In some embodiments, the percent-fill-dependent correction factor is a multiplier/divider that is selected based on the percent fill of the original sample and generates an estimated coagulation test value that is an estimate of the coagulation test value that would have been obtained for a properly filled sample. In some embodiments, the percent-fill-dependent correction factor for any particular percent fill is derived from a population average of coagulation test values at the particular percent fill normalized to coagulation test values or properly-filled samples. In some embodiments, the percent-fill-dependent correction factor is skewed to reduce the likelihood that a subject at risk of excessive or prolonged bleeding will be determined to be a normal coagulator. In some embodiments, the percent-fill-dependent correction factor is multiplied by the determined coagulation test value to generate the estimated coagulation test value. In some embodiments, the determined coagulation test value is divided by the percent-fill-dependent correction factor to generate the estimated coagulation test value.

In some embodiments, the prothombin time percent-fill-dependent correction factor is: (i) about 1.42 for a 50% full sample tube; (ii) about 1.25 for a 60% full sample tube; (iii) about 1.15 for a 70% full sample tube; (iv) about 1.08 for a 80% full sample tube; and/or (v) about 1.02 for a 90% full sample tube.

In some embodiments, the activated partial thromboplastin time percent-fill-dependent correction factor is: (i) about 1.58 for a 50% full sample tube; (ii) about 1.35 for a 60% full sample tube; (iii) about 1.20 for a 70% full sample tube;

(iv) about 1.10 for a 80% full sample tube; and/or (v) about 1.03 for a 90% full sample tube.

In some embodiments, the fibrinogen level percent-fill-dependent correction factor is: (i) about 0.41 for a 50% full sample tube; (ii) about 0.50 for a 60% full sample tube; (iii) about 0.66 for a 70% full sample tube; (iv) about 0.72 for a 80% full sample tube; and/or (v) about 0.84 for a 90% full sample tube.

In some embodiments, prothombin time percent-fill-dependent correction factors are empirically determined from a large population study performed similarly to the experiments conducted during development of embodiments herein. Based on such a study, a prothombin time level percent-fill-dependent correction factor may be selected from: (i) a value between 1.2 to 1.6 (e.g., about 1.2, about 1.25, about 1.30, about 1.35, about 1.40, about 1.45, about 1.50, about 1.55, about 1.60, or ranges therebetween) for a 50% full sample tube; (ii) a value between 1.05 to 1.45 (e.g., about 1.25, about 1.30, about 1.35, about 1.40, about 1.45, about 1.50, about 1.55, about 1.60, about 1.65, or ranges therebetween) for a 60% full sample tube; (iii) a value between 1.15 to 1.55 (e.g., about 1.15, about 1.20, about 1.25, about 1.30, about 1.35, about 1.40, about 1.45, about 1.50, about 1.55, or ranges therebetween) for a 70% full sample tube; (iv) a value between 0.90 to 1.30 (e.g., about 0.90, about 0.95, about 1.00, about 1.05, about 1.10, about 1.15, about 1.20, about 1.25, about 1.30, or ranges therebetween) for a 80% full sample tube; and/or (v) a value between 0.80 to 1.2 (e.g., about 0.80, about 0.85, about 0.90, about 0.95, about 1.0, about 1.15, about 1.20, or ranges therebetween) for a 90% full sample tube.

In some embodiments, activated partial thromboplastin time percent-fill-dependent correction factors are empirically determined from a large population study performed similarly to the experiments conducted during development of embodiments herein. Based on such a study, a activated partial thromboplastin time level percent-fill-dependent correction factor may be selected from: (i) a value between 1.4 to 1.8 (e.g., about 1.40, about 1.45, about 1.50, about 1.55, about 1.60, about 1.65, about 1.70, about 1.75, about 1.80, or ranges therebetween) for a 50% full sample tube; (ii) a value between 1.15 to 1.55 (e.g., about 1.15, about 1.20, about 1.25, about 1.30, about 1.35, about 1.40, about 1.45, about 1.50, about 1.55, or ranges therebetween) for a 60% full sample tube; (iii) a value between 1.00 to 1.40 (e.g., about 1.00, about 1.05, about 1.10, about 1.15, about 1.20, about 1.25, about 1.30, about 1.35, about 1.40, or ranges therebetween) for a 70% full sample tube; (iv) a value between 0.90 to 1.30 (e.g., about 0.90, about 0.95, about 1.00, about 1.05, about 1.10, about 1.15, about 1.20, about 1.25, about 1.30, or ranges therebetween) for a 80% full sample tube; and/or (v) a value between 0.80 to 1.2 (e.g., about 0.80, about 0.85, about 0.90, about 0.95, about 1.0, about 1.15, about 1.20, or ranges therebetween) for a 90% full sample tube.

In some embodiments, fibrinogen percent-fill-dependent correction factors are empirically determined from a large population study performed similarly to the experiments conducted during development of embodiments herein. Based on such a study, a fibrinogen level percent-fill-dependent correction factor may be selected from: (i) a value between 0.2 to 0.6 (e.g., about 0.2, about 0.25, about 0.30, about 0.35, about 0.40, about 0.45, about 0.50, about 0.55, about 0.60, or ranges therebetween) for a 50% full sample tube; (ii) a value between 0.3 to 0.7 (e.g., about 0.30, about 0.35, about 0.40, about 0.45, about 0.50, about 0.55, about 0.60, about 0.65, about 0.70, or ranges therebetween) for a 60% full sample tube; (iii) a value between 0.45 to 0.85 (e.g., about 0.45, about 0.50, about 0.55, about 0.60, about 0.65, about 0.70, about 0.75, about 0.80, about 0.85, or ranges therebetween) for a 70% full sample tube; (iv) a value between 0.50 to 0.90 (e.g., about 0.50, about 0.55, about 0.60, about 0.65, about 0.70, about 0.75, about 0.80, about 0.85, about 0.90, or ranges therebetween) for a 80% full sample tube; and/or (v) a value between 0.65 to 1.0 (e.g., about 0.65, about 0.70, about 0.75, about 0.80, about 0.85, about 0.90, about 0.95, about 1.0, or ranges therebetween) for a 90% full sample tube.

In some embodiments, the blood sample is obtained from a subject (e.g., a human subject, a non-human animal subject (e.g., bovine subject, porcine subject, canine subject, feline subject, ovine subject, equine subject, simian subject, etc.)). In some embodiments, the subject is a candidate for treatment with an anticoagulant agent. In some embodiments, the anticoagulant agent is selected from heparin, low molecular weight heparin, warfarin, an inhibitor of factor Xa, a directly acting oral anticoagulant, and a direct thrombin inhibitor. In some embodiments, the human subject presents with acute stroke symptoms.

DEFINITIONS

Figure 1:
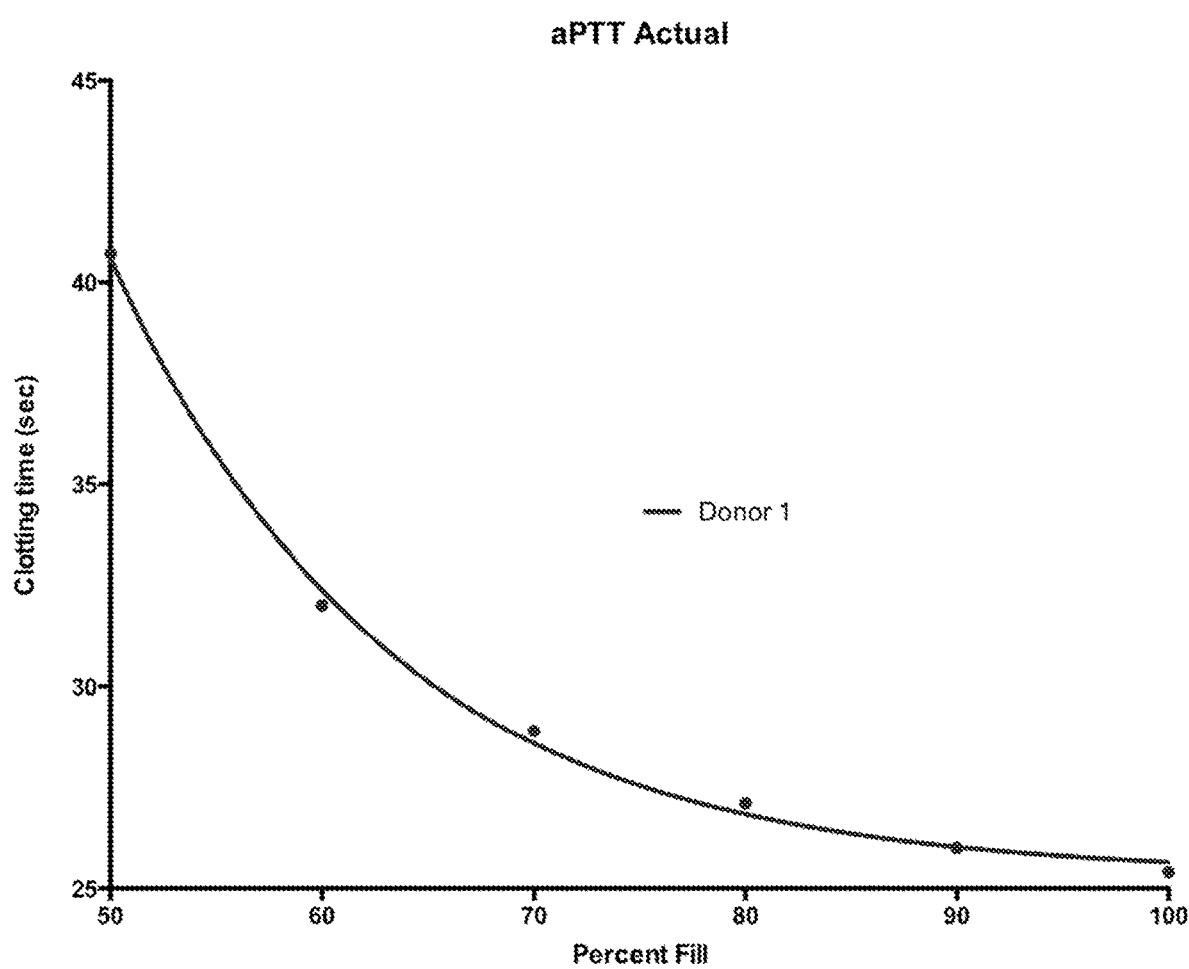
FIG. 1 shows aPTT measurements for underfilled samples (50%, 60%, 70%, 80%, and 90%) in comparison with a properly filled sample (100%) from an exemplary donor subject.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a sample tube" is a reference to one or more sample tubes and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "substantially" means that the recited characteristic, parameter, and/or value need not be achieved exactly, but that deviations or variations, including for example, tolerances, measurement error, measurement accuracy limitations and other factors known to skill in the art, may occur in amounts that do not preclude the effect the characteristic was intended to provide.

The terms "about" and "approximately" allows for a degree of variability in a value or range. As used herein, the term "about" refers to values within 10% of the recited value or range (e.g., about 50 is the equivalent of 45-55). "About" also includes narrower ranges (e.g., within 9%, within 8%, within 7%, within 6%, within 5%, within 4%, within 3%, within 2%, within 1%) that may be independently claimed.

As used herein, the term "percent fill" refers to the volume of a sample (e.g., in a sample tube) relative to a properly-filled sample. A sample with a percent fill of 75%, has a volume that is 75% of a properly-filled sample.

As used herein, the term "anticoagulants," or colloquially referred to as "blood thinners," refers to agents that that prevent or reduce coagulation of blood, prolonging the clotting time. Exemplary anticoagulants agents include, but are not limited to, heparin and derived substances (e.g., low molecular weight heparin), warfarin (Coumadin) and other coumarins (vitamin K antaganists, such as, acenocoumarol, phenprocoumon, atromentin, phenindione, etc.), inhibitors of factor Xa (e.g., Idraparinux, Fondaparinux, etc.), directly acting oral anticoagulants (e.g., dabigatran, rivaroxaban, apixaban, edoxaban, betrixaban, etc.), and direct thrombin inhibitors (e.g., hirudin, bivalirudin, lepirudin, desirudin, argatroban, inogatran, melagatran (and its prodrug ximelagatran), dabigatran, etc.).

DETAILED DESCRIPTION

Provided herein are methods for generating an estimated coagulation test result from an underfilled sample tube.

Having the correct volume of sample in collection tubes is an important quality control measure for clinical testing. However, this issue is particularly important in samples drawn for coagulation testing, due to the nature of the collection tubes. In order to provide reversible prevention of coagulation, the current standard is for all blood specimens sent for coagulation testing to be drawn into tubes with sodium citrate. The appropriate ratio for blood anticoagulation is 1 part citrate anticoagulant to 9 parts blood. Improperly filled sample tubes disrupt this ratio and can cause a significant alteration in PT, international normalized ratio (INR), and aPTT. This is particularly true for under-filled specimens. Though differing methodologies have produced somewhat varying results, statistically significant alterations in many commonly used coagulation tests, including PT, aPTT, fibrinogen, and INR occur when the fill volume is <90% of the proper volume. The aPTT appears to be more sensitive to underfilling volumes than the PT. The Clinical & Laboratory Standards Institute (CLSI) recommends that all tubes used for coagulation testing be filled to within 10% of their proper fill value and that tubes with 3.2% sodium citrate (105-109 mM) are preferred over those with 3.8% sodium citrate (129 mM).

Discarding all samples that are not filled to within this narrow range results in numerous drawbacks. The time needed for a practitioner to re-draw a sample adds to the workload, particularly if the patient has gone to a different part of the facility. Patients without already existing peripheral blood access need an additional needlestick, which causes additional discomfort and increases the risk of untoward effects. In some cases, particularly in an outpatient setting, the patient may have already left the area and is unavailable for an additional draw, resulting in an inability to get a result from the lab. Potentially most harmful, however, is the delay in obtaining results when a sample must be discarded and another draw is needed. A further delay of even one-half hour may at times be pivotal, when such delay would, for example put a patient manifesting acute stroke symptoms beyond the deadline for initiation of the clot-dissolving drug, tissue plasminogen activator (an initiation which needs to occur within 3 hours (4.5 hours in some patient populations). A delay in obtaining coagulation lab results could result in the treatment not being administered within the therapeutic timeframe.

Although there have been prior studies on the effects that underfilling sample tubes have on coagulation testing, there is no current methodology in the field for correcting for these effects to provide an estimation of what the values of these tests would be for a properly filled sample. The ability to "correct" the values from an underfilled sample, even if only as an estimate, would allow clinicians to more rapidly assess the clinical state of their patients and treat if appropriate and would also allow them to decide if the need for a more exact measurement of coagulation testing warrants the additional time and needlestick necessary to create a properly prepared sample. Experiments were conducted during development of embodiments herein to determine whether correcting the volume of underfilled samples generated a consistent effect on PT, APTT and fibrinogen levels, which would allow for the calculation of an estimate for the results of these tests on a properly filled specimen.

In some embodiments, provided herein are methods for the calculation of commonly used coagulation test values from underfilled samples. Experiments conducted during development of embodiments herein demonstrate significant accuracy of the methods herein for fill volumes of greater than or equal to 50%. The calculation methods herein avoid miscalling hypocoagulable patients as "normal" in all clinically significant tests performed. Avoiding this sort of error is important for the potential use of this method in both inpatient and outpatient settings. In an inpatient setting, avoiding mischaracterizing a hypocoagulable patient as "normal" could cause a clinician to administer an anti-thrombotic agent (anticoagulant, anti-platelet, or, as in the case of tPA anti-fibrinolytic) to a patient who is already hypocoagulable, further increasing the risk of bleeding.

Experiments conducted during development of embodiments herein demonstrate the feasibility of performing coagulation testing on underfilled patient samples by correcting their volume and then using an equation to predict the actual value (e.g., the value that would have been measured for a properly-filled sample).

In some embodiments, a coagulation test is performed on a blood sample from a subject. In some embodiments, a coagulation test is performed on a blood sample from a subject to assist in deciding whether to administer a particular treatment (e.g., antithrombotic, anticoagulant, etc.) to the subject. For example, in patients presenting with acute ischemic stroke, rapid (e.g., <6 hours, <5 hours, <4 hours, <3 hours, <2 hours, <1 hour, etc.) treatment with antithrombotics is recommended; however, in subjects with an elevated risk of bleeding (e.g., high PT, high aPTT, low fibrinogen levels, etc.), the use of antithrombotic therapy is contraindicated. Therefore, in order to rapidly clear a subject for the use of antithrombotic therapy for the treatment of acute ischemic stroke (or other conditions), anticoagulant testing is ordered in order to assess the capacity of the subject to stop bleeding. In such a situation, an underfilled sample tube can delay the testing beyond the timescale for useful treatment. As such, provided herein are methods for generating an estimated coagulation test result from an underfilled sample tube. In some embodiments, the estimated result provides clinicians with an assessment of whether a subject is likely to be a bleeding risk.

Anticoagulants are drugs for preventing blood coagulation (thrombosis) caused by either foreign matter (artificial valve) in the cardiovascular system, arrhythmia, or a variety of imbalances of the patient's procoagulant and natural anticoagulant levels. Anticoagulant therapy is used for the treatment and prevention of deep vein thrombosis, pulmonary embolism, heart diseases, cerebral embolism, etc., and after artificial heart valve replacement. Typical drugs that are used in such anticoagulant therapy include heparin, a kind of acidic polysaccharide having sulfate groups, which is a strong inhibitor of blood coagulation, and vitamin K antagonist warfarin. In addition, fraxiparine, enoxaparin, etc., are also used. Heparin binds to antithrombin III to show a rapid anticoagulant effect. Antithrombin III is also called heparin coenzyme and inhibits various serine protease coagulation factors such as thrombin and factor Xa. Because an overdose of heparin reduces rather than increases the activity of antithrombin, thus resulting in the risk of thrombosis, low-dose heparin is used through intravenous injection or subcutaneous injection, and the dose thereof is determined while the degree of blood coagulation in a patient is checked whenever needed. Vitamin K antagonists include warfarin and dicumarol.

EXPERIMENTAL

All experimental samples were from clinical specimens that were sent to the coagulation laboratory at below the standard acceptable minimum volume (<90%). As per hospital protocol, the ordering physician was informed that the sample volume was inadequate, and an additional blood tube was requested. Blood samples from eight healthy volunteers were used to make the standard curves that would be used to calculate the estimated test vales for the patient samples. Blood was collected from each of these volunteers and was used to create tubes that were filled to 50, 60, 70, 80, 90 and 100 percent of the proper volume. All underfilled samples were brought up to the proper volume using imidazole buffered saline (0.34 g imidazole and 0.585 g of NaCl in 100 mL of distilled water, pH 7.3).

Figure 2:
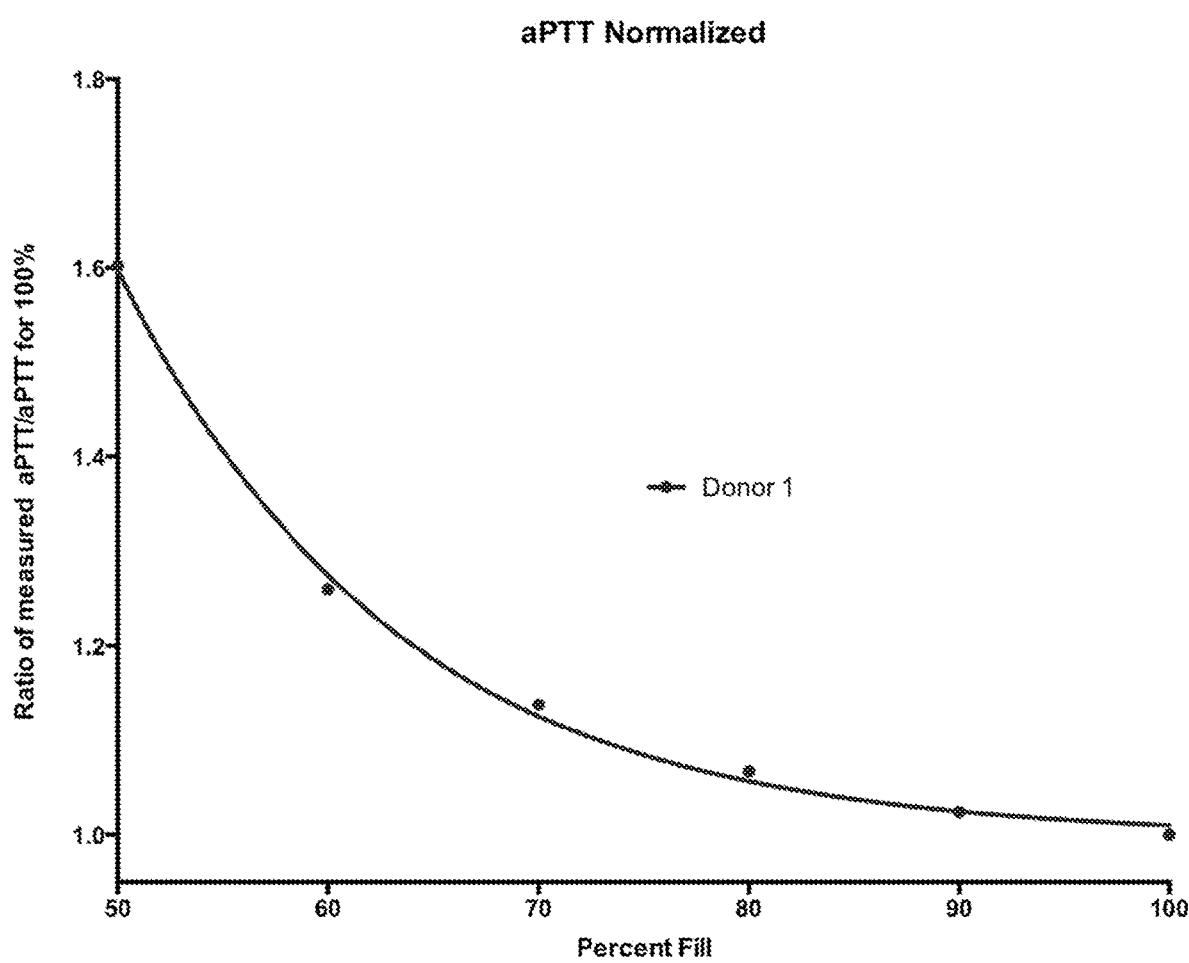
FIG. 2 shows normalized aPTT values (divided by the 100% measurement) from the underfilled samples (50%, 60%, 70%, 80%, and 90%), in comparison with the properly filled sample (100%) from the same exemplary donor subject.
Figure 3:
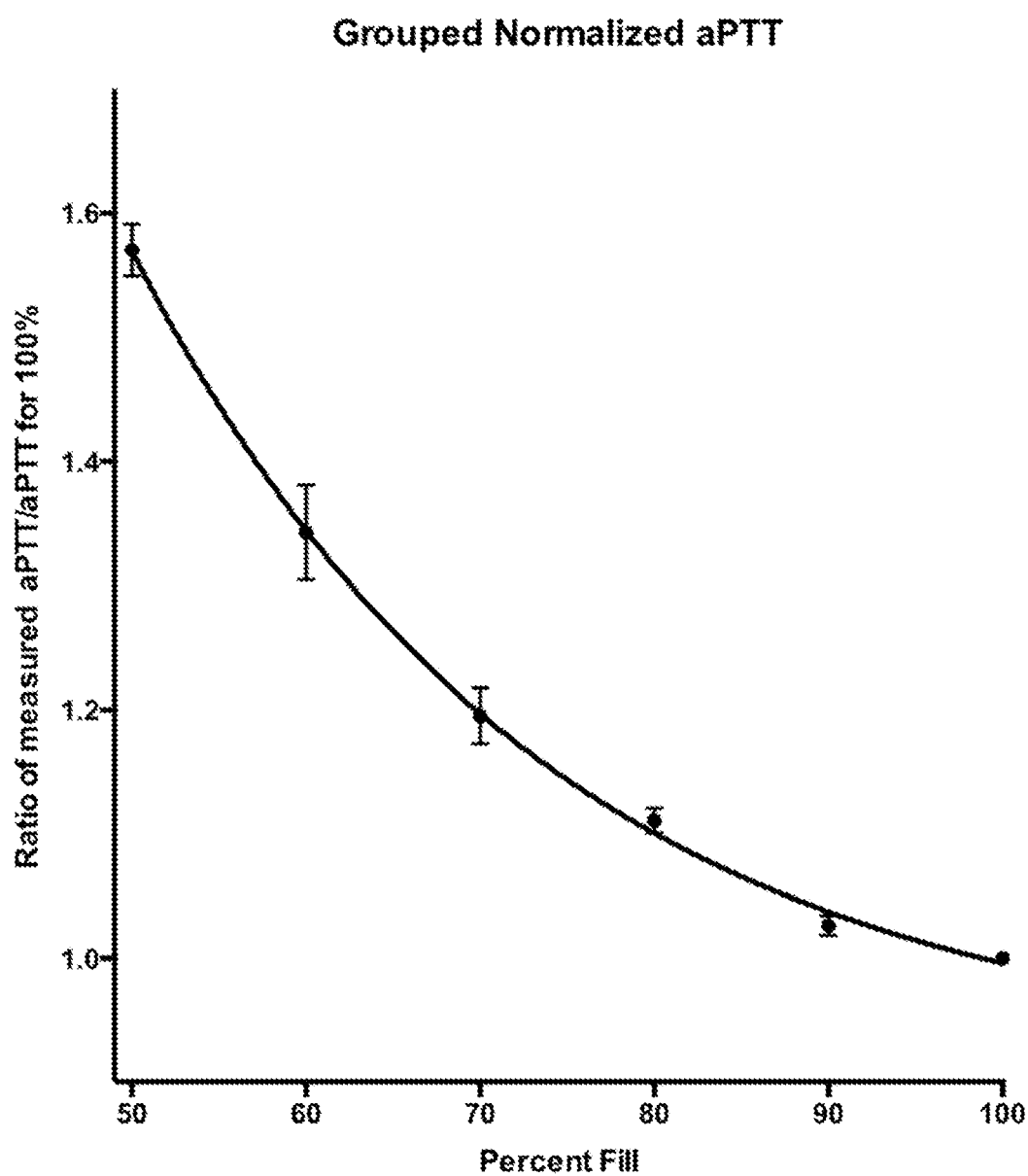
FIG. 3 shows grouped normalized aPTT measurements from underfilled samples (50%, 60%, 70%, 80%, and 90%), and the respective properly filled samples, obtained by averaging the normalized aPTT values from a group of donor subjects.
Figure 4:
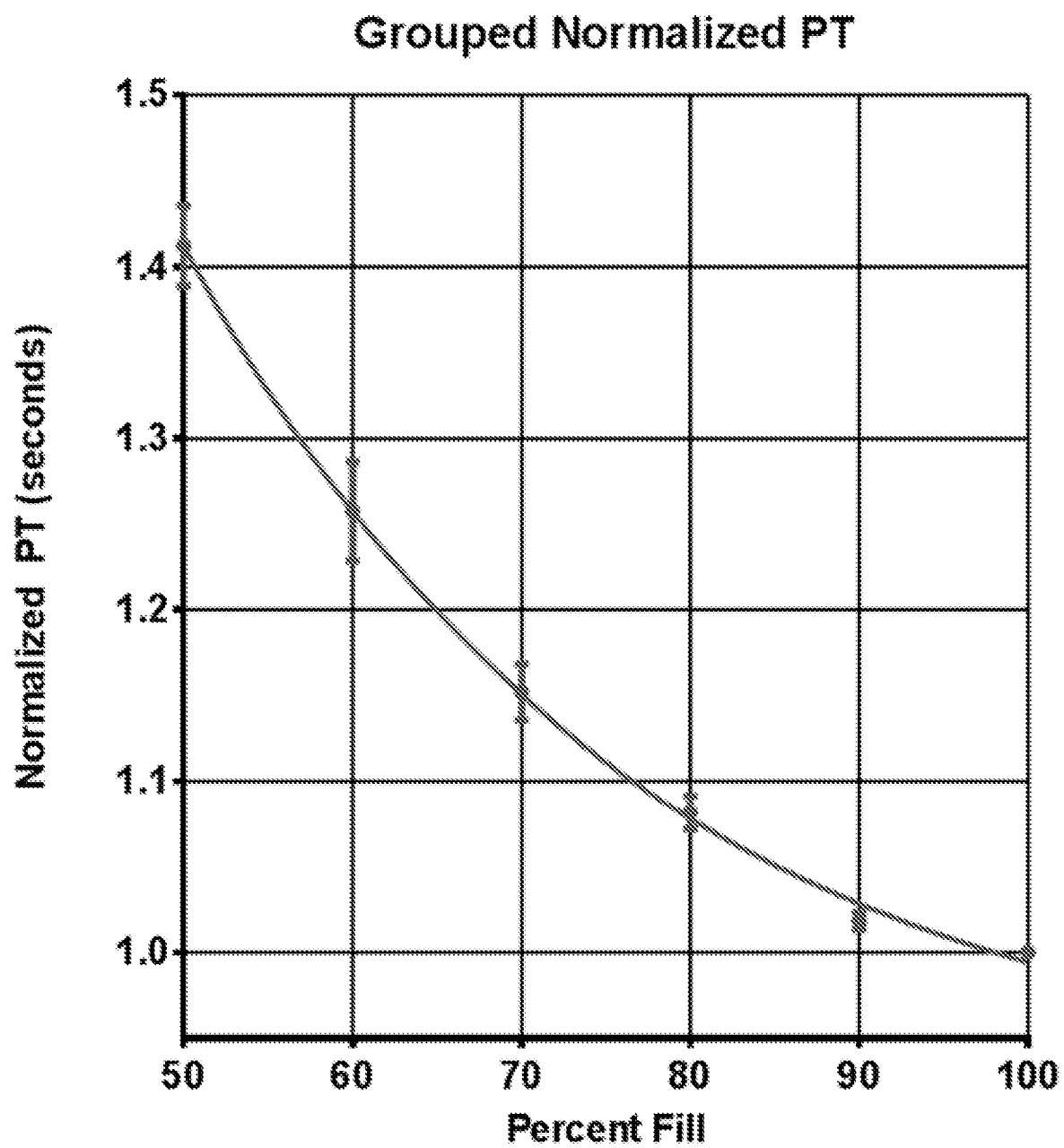
FIG. 4 shows grouped normalized PT measurements from underfilled samples (50%, 60%, 70%, 80%, and 90%), and the respective properly filled samples, obtained by averaging the normalized PT values from a group of donor subjects.
Figure 5:
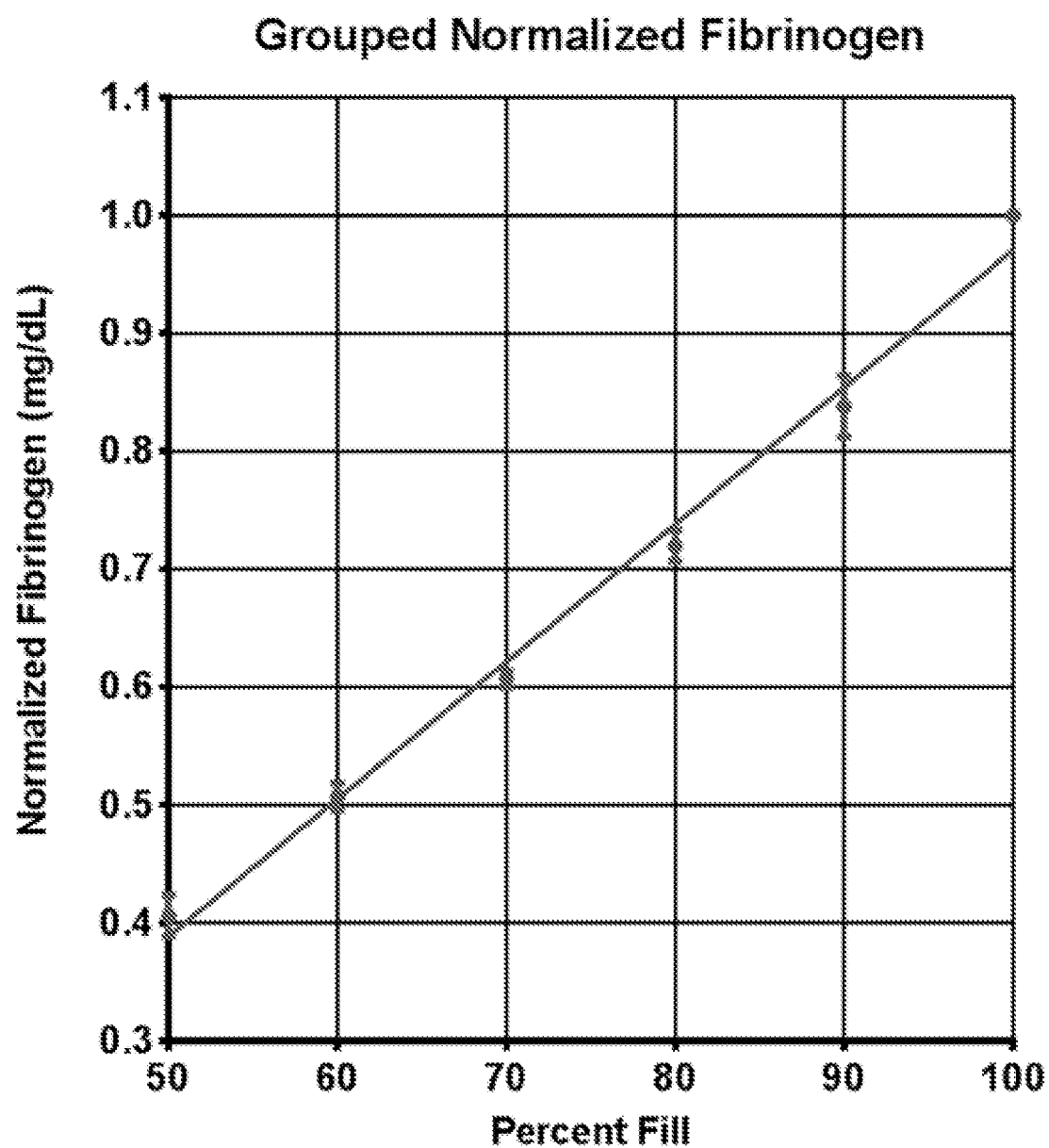
FIG. 5 shows grouped normalized fibrinogen measurements from underfilled samples (50%, 60%, 70%, 80%, and 90%), and the respective properly filled samples, obtained by averaging the normalized fibrinogen values from a group of donor subjects.

Prothrombin time, activated partial thromboplastin time, and fibrinogen levels were determined using the STA-R Evolution instrument (Stago) according to a standard protocol for clinical samples. For the training set of normal donors, raw aPTT values were first obtained from each subject for tubes filled to the differing amounts of completion (50%, 60%, 70%, 80%, 90% and 100%), with 100% being the normally intended volume. An exemplary aPTT curve for a single donor is depicted in FIG. 1 (similar curves for other donors and other markers (e.g., PT, fibrinogen) were obtained likewise). Next, each value was "normalized" to the 100% measurement on a donor-by-donor basis. For the aPTT donor data depicted in FIG. 1, the 100% value was 25.4 seconds; so, each of the measured values was divided by 25.4, the results of which are depicted in FIG. 2 (similar curves for other donors and other markers (e.g., PT, fibrinogen) were obtained likewise). The calculated ratios at each of the dilutions for each of the subjects were then combined to generate a normalized curve for the group, exemplary results for aPTT are depicted in FIG. 3 (similar curves for other donors and other markers (e.g., PT, fibrinogen) were obtained likewise). Exemplary grouped normalized curves for PT and fibrinogen are depicted in FIGS. 4-5. For prothrombin time and activated partial thromboplastin time, the curve was well described mathematically by exponential decay. For the fibrinogen concentration, the curve was linear.

Figure 6:
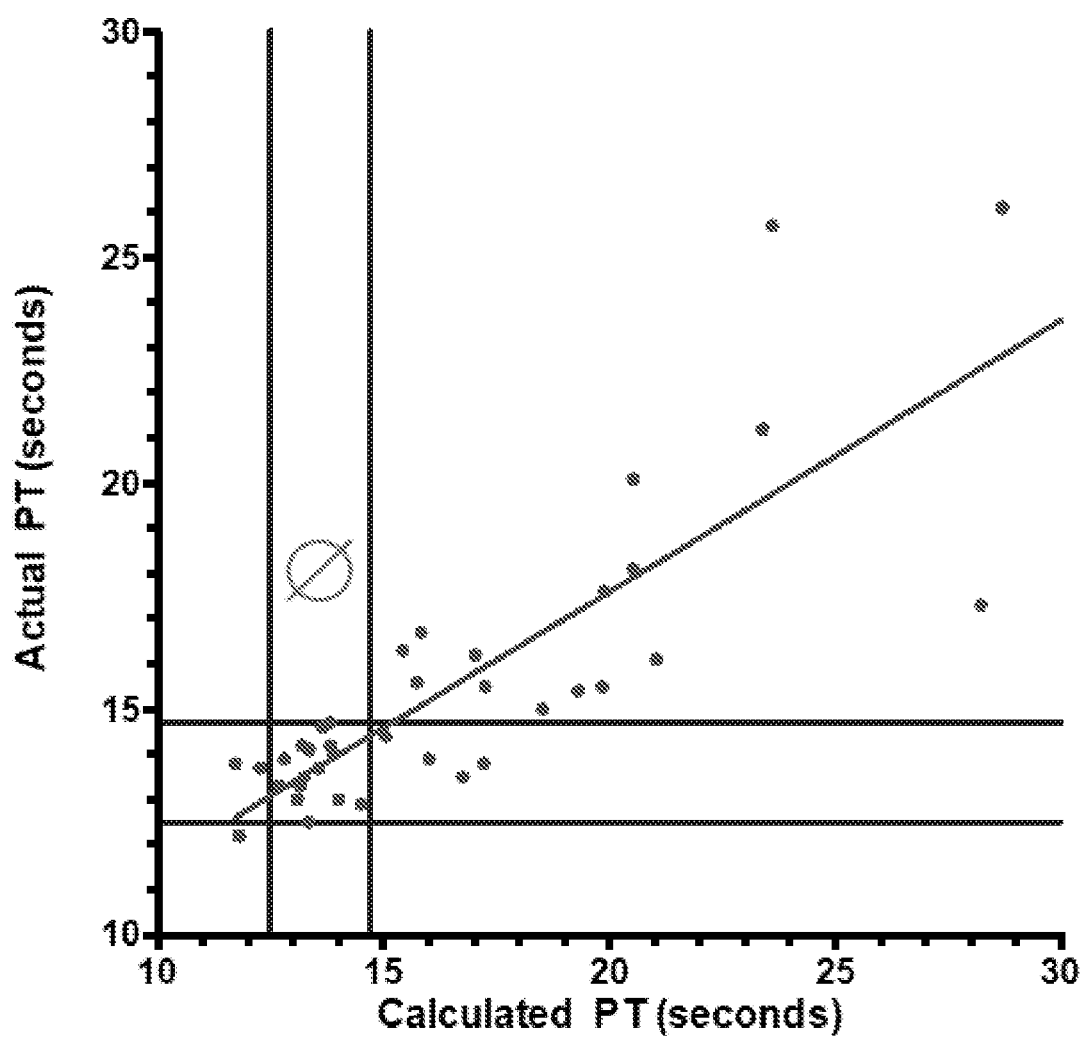
FIG. 6 shows a graph of calculated PT values (estimated from underfilled samples) vs. actual PT values (obtained from properly-filled samples). Each point represents an estimated and actual PT value for a single subject. The horizontal lines represent the upper and lower limits for the "normal" PT range. The vertical lines correspond the upper and lower limits for the "normal" PT range for the estimated values. The "ø" symbol represents the segment of the plot in which a subject who actually exhibits a prolonged PT would have been estimated to have a normal PT.
Figure 7:
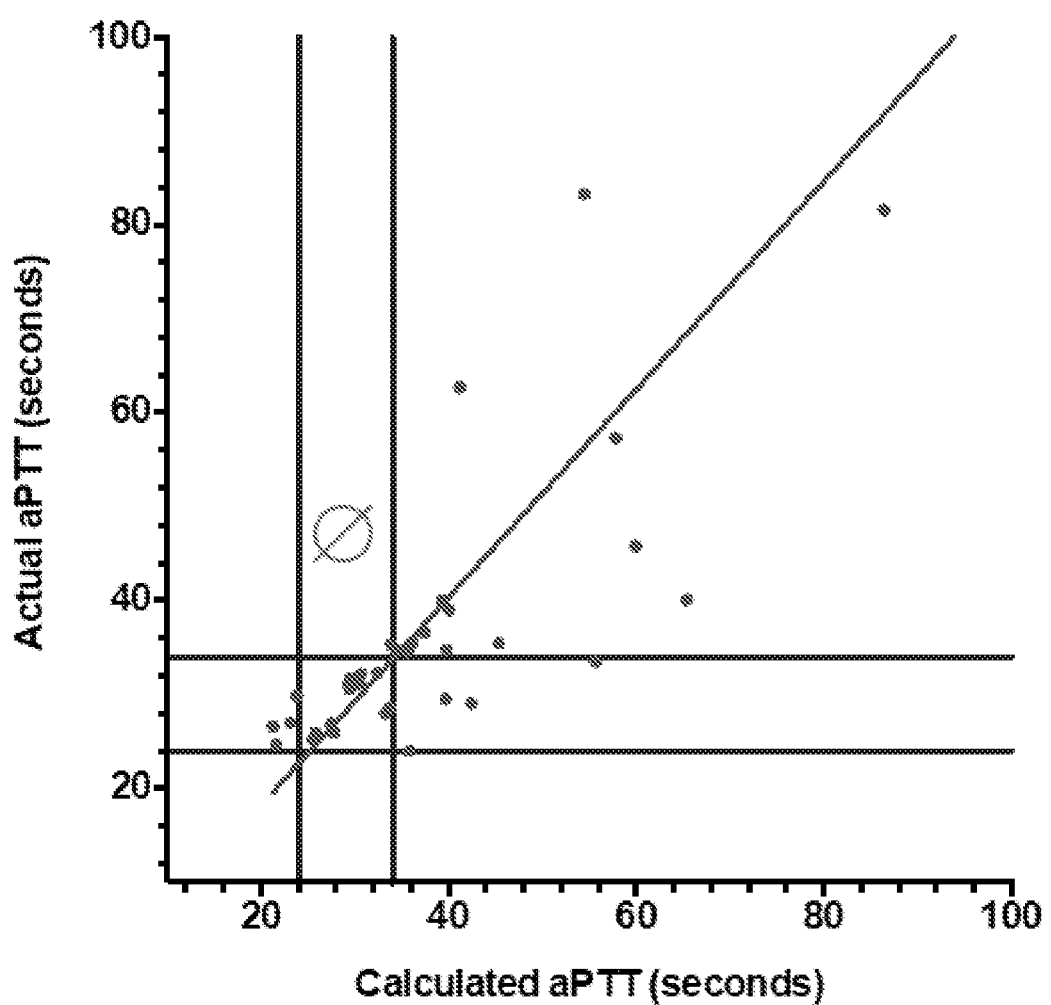
FIG. 7 shows a graph of calculated aPTT values (estimated from underfilled samples) vs. actual aPTT values (obtained from properly-filled samples). Each point represents an estimated and actual aPTT value for a single subject. The horizontal lines represent the upper and lower limits for the "normal" aPTT range. The vertical lines correspond the upper and lower limits for the "normal" aPTT range for the estimated values. The "ø" symbol represents the segment of the plot in which a subject who actually exhibits a prolonged aPTT would have been estimated to have a normal aPTT.
Figure 8:
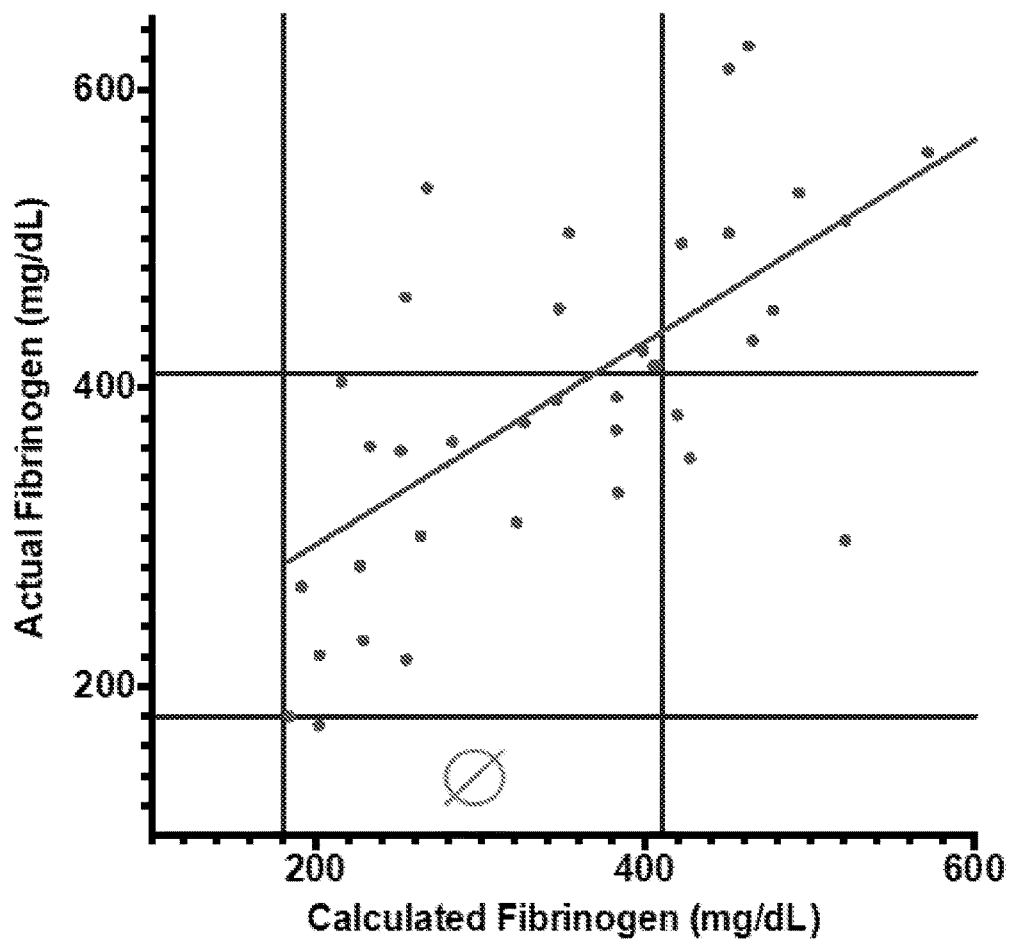
FIG. 8 shows a graph of calculated fibrinogen values (estimated from underfilled samples) vs. actual fibrinogen values (obtained from properly-filled samples). Each point represents an estimated and actual fibrinogen value for a single subject. The horizontal lines represent the upper and lower limits for the "normal" fibrinogen range. The vertical lines correspond the upper and lower limits for the "normal" fibrinogen range for the estimated values. The "ø" symbol represents the segment of the plot in which a subject who actually exhibits a low fibrinogen would have been estimated to have a normal fibrinogen.

From the group normalized results, a correction factor was obtained from the mathematically determined curve fits for each percent fill (e.g., an aPTT correction factor of 1.195 for a 70% fill). The correction factor is used to correct the results obtained from underfilled samples. For example, the measured aPTT on a 70% sample (that had been diluted with buffered saline to 100%) from a particular subject was 36.6 seconds. An estimated aPTT was calculated by dividing the measured time by the correction factor for 70% (1.195), yielding an estimated aPTT of 30.6 seconds. Subsequently, the aPTT test was rerun on a properly filled sample tube, and an aPTT of 32.2 seconds was measured. 34 seconds is the upper limit of a normal for the aPTT test; therefore, for this exemplary subject, the estimated aPTT correctly determined that the subject was in the normal range. The predicted correction to 30.6 seconds, which is clearly very close also to the 32.2 seconds, had the virtue of bringing an otherwise spuriously prolonged aPTT back into the normal range. Results plotting calculated (estimated) values vs. actual values (measured on a properly-filled sample tube) are depicted in FIGS. 6-8.

Although there are instances in which the "calculated" PT values are both above and below the actual values, there are no situations in which the "calculated" PT indicated that a patient was normally coagulable when the patient was in actuality hypocoagulable. This is important because the purpose of the "calculated" value is to help guide clinical decision making while a new sample is collected/analyzed. Avoiding any points in the ø zone means that clinicians getting a "calculated" value could, at the minimum, feel comfortable that a patient with a normal calculated value is not hypocoagulable and could administer appropriate interventions (such as TPA) as a result. Also notably, there does not appear to be a significant drop-off in the accuracy of the calculations as one goes to lower fill volumes, down to a limit of 50%.

The invention claimed is:

1. A method for calculating an estimated coagulation test value for an underfilled blood sample with an actual volume that is less than a target volume, comprising:
   (a) determining a percent fill of the sample, wherein the percent fill is equal to the actual volume divided by the target volume;
   (b) correcting the actual volume to produce a corrected sample with a volume equal to the target volume;
   (c) performing a coagulation test to obtain a determined coagulation test value;
   (d) applying a percent-fill-dependent correction factor to the determined coagulation test value to generate the estimated coagulation test value.

2. The method of claim 1, wherein the percent fill is less than 90%.

3. The method of claim 2, wherein the percent fill is 50% to 90%.

4. The method of claim 1, wherein correcting the sample volume comprises adding aqueous buffer or other diluent to the sample.

5. The method of claim 4, wherein correcting the sample volume comprises adding imidazole buffered saline to the sample.

6. The method of claim 5, wherein the imidazole buffered saline comprises about 0.34 g imidazole and about 0.585 g of NaCl per 100 mL of distilled water and is at about pH 7.3.

7. The method of claim 1, wherein correcting the sample volume comprises bringing to volume of the sample to 90-110% fill.

8. The method of claim 7, wherein correcting the sample volume comprises bringing to volume of the sample to 99-101% fill.

9. The method of claim 8, wherein correcting the sample volume comprises bringing to volume of the sample to 100% fill.

10. The method of claim 1, wherein performing the coagulation test comprises determining one or more of prothrombin time (PT), activated partial thromboplastin time (aPTT), thrombin time (TT), fibrinogen level, and international normalized ratio (INR).

11. The method of claim 1, wherein the determined coagulation test value is the result obtained by performing the coagulation test as if the corrected sample were a properly filled sample.

12. The method of claim 1, wherein the percent-fill-dependent correction factor is a multiplier/divider that is selected based on the percent fill of the original sample and generates an estimated coagulation test value that is an estimate of the coagulation test value that would have been obtained for a properly filled sample.

13. The method of claim 12, wherein the percent-fill-dependent correction factor for any particular percent fill is derived from a population average of coagulation test values at the particular percent fill normalized to coagulation test values or properly-filled samples.

14. The method of claim 13, wherein the percent-fill-dependent correction factor is skewed to reduce the likelihood that a subject at risk of excessive or prolonged bleeding will be determined to be a normal coagulator.

15. The method of claim 13, wherein the percent-fill-dependent correction factor is multiplied by the determined coagulation test value to generate the estimated coagulation test value.

16. The method of claim 13, wherein the determined coagulation test value is divided by the percent-fill-dependent correction factor to generate the estimated coagulation test value.

17. The method of claim 16, wherein the prothrombin time percent-fill-dependent correction factor is:
   (i) about 1.42 for a 50% full sample tube;
   (ii) about 1.25 for a 60% full sample tube;
   (iii) about 1.15 for a 70% full sample tube;
   (iv) about 1.08 for a 80% full sample tube; and/or
   (v) about 1.02 for a 90% full sample tube.

18. The method of claim 16, wherein the activated partial thromboplastin time percent-fill-dependent correction factor is:
   (i) about 1.58 for a 50% full sample tube;
   (ii) about 1.35 for a 60% full sample tube;
   (iii) about 1.20 for a 70% full sample tube;
   (iv) about 1.10 for a 80% full sample tube; and/or
   (v) about 1.03 for a 90% full sample tube.

19. The method of claim 16, wherein the fibrinogen level percent-fill-dependent correction factor is:
   (i) about 0.41 for a 50% full sample tube;
   (ii) about 0.50 for a 60% full sample tube;
   (iii) about 0.66 for a 70% full sample tube;
   (iv) about 0.72 for a 80% full sample tube; and/or
   (v) about 0.84 for a 90% full sample tube.

20. The method of claim 1, wherein the blood sample is obtained from a human subject.

21. The method of claim 20, wherein the human subject is a candidate for treatment with an anticoagulant agent.

22. The method of claim 21, wherein the anticoagulant agent is selected from heparin, low molecular weight heparin, warfarin, an inhibitor of factor Xa, a directly acting oral anticoagulants, and a direct thrombin inhibitor.

23. The method of claim 19, wherein the human subject presents with acute stroke symptoms.

* * * * *